United States Patent
Heiligenstein

(10) Patent No.: US 11,860,074 B2
(45) Date of Patent: Jan. 2, 2024

(54) EMBEDDING MEDIUM OF BIOLOGICAL SAMPLE FOR ITS IMAGING BY LIGHT AND/OR ELECTRON MICROSCOPY

(71) Applicant: CRYOCAPCELL, Paris (FR)

(72) Inventor: Xavier Heiligenstein, Paris (FR)

(73) Assignee: CRYOCAPCELL, Paris (FR)

( * ) Notice: Subject to any disclaimer, the term of this patent is extended or adjusted under 35 U.S.C. 154(b) by 771 days.

(21) Appl. No.: 16/980,560

(22) PCT Filed: Mar. 15, 2019

(86) PCT No.: PCT/EP2019/056584
§ 371 (c)(1),
(2) Date: Sep. 14, 2020

(87) PCT Pub. No.: WO2019/175407
PCT Pub. Date: Sep. 19, 2019

(65) Prior Publication Data
US 2021/0003487 A1    Jan. 7, 2021

(30) Foreign Application Priority Data

Mar. 16, 2018   (EP) .................................... 18305293

(51) Int. Cl.
*G01N 1/36* (2006.01)
*C08F 265/06* (2006.01)
(Continued)

(52) U.S. Cl.
CPC ............. *G01N 1/36* (2013.01); *C08F 265/06* (2013.01); *C08K 5/098* (2013.01); *G02B 21/33* (2013.01);
(Continued)

(58) Field of Classification Search
CPC .. G01N 1/30; G01N 1/36; G01N 1/42; G01N 2001/364; G02B 21/33; C08K 5/098
See application file for complete search history.

(56) References Cited

FOREIGN PATENT DOCUMENTS

KR         19980063873 A    * 12/1997
KR         100707560 B1     * 10/2005
(Continued)

OTHER PUBLICATIONS

International Search Report dated Jun. 11, 2019 and Written Opinion in corresponding International application No. PCT/EP2019/056584; 9 pages.

*Primary Examiner* — David E Smith
*Assistant Examiner* — Hsien C Tsai
(74) *Attorney, Agent, or Firm* — Maier & Maier, PLLC

(57) ABSTRACT

The present invention relates to the field of microscopy, preferably electron microscopy. Especially, the present invention concerns an embedding medium for imaging a biological sample by microscopy comprising:
  from 60% to 99% wt. of a glycol dimethacrylate selected from alkylene glycol dimethacrylate and/or oligo(alkylene glycol) dimethacrylate;
  from 0% to 38% wt. of a polyalkylene glycol diacrylate or of a polyalkylene glycol methacrylate; said polyalkylene glycol diacrylate or polyalkylene glycol methacrylate being optionally substituted by at least one hydrophilic group such as hydroxyl, amino, or an oxo group;
  at least one additive, preferably comprising at least one heavy metal salt or lanthanide salt; and
  from 0.1% to 2% wt. of a radical polymerization initiator.
The present invention also refers to the electro-conductive material resulting from the polymerization of the embedding medium of the invention, and the process and kits of preparation thereof; said material embedding at least one biological sample.

(Continued)

The present invention also relates to a method for imaging by microscopy, a biological sample comprising using the embedding medium and/or the electro-conductive material of the invention.

19 Claims, 3 Drawing Sheets

(51) Int. Cl.
    *C08K 5/098*     (2006.01)
    *G02B 21/33*     (2006.01)
    *H01J 37/20*     (2006.01)

(52) U.S. Cl.
    CPC ........ H01J 37/20 (2013.01); *G01N 2001/364* (2013.01)

(56) References Cited

FOREIGN PATENT DOCUMENTS

| | | |
|---|---|---|
| KR | 100707560 B1 | 4/2007 |
| WO | 2015/038940 A1 | 3/2015 |
| WO | 2015/160699 A1 | 10/2015 |
| WO | 2017/078177 A1 | 5/2017 |

\* cited by examiner

EMBEDDING MEDIUM OF BIOLOGICAL SAMPLE FOR ITS IMAGING BY LIGHT AND/OR ELECTRON MICROSCOPY

FIELD OF INVENTION

The present invention relates to the field of microscopy, preferably the field of light and/or electron microscopy. Especially, the present invention concerns an embedding medium for imaging a biological sample by microscopy. The embedding medium of the invention refers to a composition comprising or being constituted of a mixture of (i) glycol dimethacrylate, (ii) polyalkylene glycol diacrylate and/or polyalkylene glycol methacrylate, and (iii) an initiator. The present invention also refers to the electro-conductive and/or bio-preserving material resulting from the polymerization of the embedding medium of the invention, and the process and kits of preparation thereof; said material embedding at least one biological sample.

The present invention also relates to a method for imaging by microscopy, a biological sample comprising the use of the embedding medium and/or the electro-conductive material of the invention.

BACKGROUND OF INVENTION

Microscopy refers to a set of techniques for observing objects and areas of objects that cannot be achieved by the naked eye. Among the well-known microscopy techniques, electron microscopy is useful for the observation of biological material. This technique generates an amplitude or phase contrast imagery thanks to the diffraction, the reflection or refraction of either electron beams, or an electromagnetic radiation, that directly interacts with the sample to be observed.

To date, obtaining a good amplitude contrast is made possible only by the addition of contrast agents consisting essentially of heavy metal salts and fixatives (such as aldehydes).

High resolution electron microscopy visualization of any sample also implies complex preparation steps like fixation so that the sample is the closest to native during the microscopy analysis while remaining protected from the high vacuum of an electron microscope.

Fixation of the biological material can be achieved either chemically (addition of fixatives such as aldehydes) or physically (ultrafast freezing approaches to achieve vitrification or amorphous immobilization of the water content of a biological material).

Especially, for achieving the observation of native biological material after fixation, embedding methods have been developed to replace water of the fixed biological sample by polymer resin in order to protect it from the vacuum while strengthening it to allow thin sectioning by ultramicrotomy.

However, using fixatives and contrasting agents causes: 1) contaminated waste reprocessing problems during sample preparation, 2) biological properties alteration and 3) poor evacuation of electronic charges during imaging. Indeed, fixatives and heavy metal salt are toxic, mutagenic, carcinogenic and/or radioactive. They partially or totally alter biological properties of fluorescence emission upon stimulation or protein activity or mask antigens for immuno-detection. Furthermore, the heavy metal salts only capture electrons during imaging but do not allow to discharge the electron charges accumulating on the sample surface during the realization of the microscopic cliché. As a result, a local accumulation of electronic charges on the surface of the sample is obtained leading to the formation of a halo surrounding the sample and preventing proper imaging. Consequently, interpreting the clichés is made difficult.

For example, in transmission electron microscopy (TEM) or electron tomography, this hyper-loading dramatically changes the focal plane and the images are obtained at the wrong focus. In scanning electron microscopy (SEM), the electronic overload provides a white halo at the surface of the sample.

Alternative solutions have been developed. One solution is to reduce the charge effect created by the use of heavy metal salts in large excess and by refining low-electron imaging parameters (Deerinck et al., 2010). However, this method is very aggressive, is not adapted to a wide variety of biological samples and imposes to work at room temperature, preventing the best ultrastructure preservation achieve by cryo-fixation. In particular, this method makes it possible to highlight mostly the membranes or cell walls but causes heavy extraction, excluding all information relating to the rest of the biological content.

Another solution consists in associating the use of heavy metal salts with a thin carbon film or metal deposition by evaporation, the latter making it possible to provide the electronic discharge. However, this method requires additional steps to prepare the sample and evacuates the charge only at the periphery of the sample. In addition, the amount of heavy metal salts still causes the subsequent reprocessing of waste.

There is therefore a need to provide a more efficient process for preparing biological samples for electron microscopy imaging. In particular, there is a need to provide more efficient biological material embedding media able to reduce the need of contrasting agents and/or their biological effects while maximizing the contrast of the sample during its imaging by electron microscopy to obtain the best quality images possible.

Among commercially available resins, Lowicryl® resins have the advantage of subliming little under the action of the electron beam. Furthermore, the precursor solutions of these resins (i.e. before polymerization) remain fluid at temperatures down to −35° C. or −70° C. depending on the products, thus making them compatible with fast freezing and cryo-substitution methods used for the analysis of the vitrified biological sample. Fast freezing is considered to date as the closest to native fixation procedure of biological material and is widely used in qualitative and quantitative analysis.

However, Lowicryl® resins are not electro-conductive and lead to unsatisfactory observation of the sample during analysis by electron microscopy, especially if too little amount of contrasting agent is used during the sample preparation.

Therefore, there is also a need to provide biological material embedding media able to effectively evacuate the accumulated electron charges at the surface of the sample and/or of the embedding medium during the imaging in the electron microscope after embedding at room temperature or at cryo temperatures. There is also a need to provide more efficient biological material embedding media able to maintain good stability and/or physical integrity during its electron microscope imaging. There is also a need to provide embedding media able to drastically reduce the amount of heavy metal salts or lanthanide salt used. Therefore, there is also a need to provide biological material embedding media able of preserve the best ultra-structure along the microscopy analysis.

To optimize further the use of electron microscopy in biological studies, fluorescence microscopy allows efficient targeting of the biological sample. The use of fixatives and/or contrasting agents notably reduces the fluorescence and the native properties of proteins embedded in the resin. Epoxy resins for example interact with amine groups of proteins, preventing their further ability to act as proteins. Lowicryl® resins or acrylate resins do not cross-react with biological matter and protect their resonating properties.

Thus, there is a need for providing a non-biointeracting embedded medium that efficiently preserves the native fluorescence of the embedded biological sample while preserving contrast for potential electron microscopy (EM).

Surprisingly, the Applicant has demonstrated that a hydrophilic resin derived from the polymerization of a monomer mixture selected from glycol dimethacrylate, a polyalkylene glycol diacrylate and/or polyalkylene glycol methacrylate, provides an efficient embedding medium solving the problems of the prior art described above.

Advantageously, the ultrastructure as well as the fluorescence of the biological sample included in the embedding medium of the invention are preserved. Advantageously, the imaging contrast obtained with the embedding medium of the invention is greater than those achieved by the use of commercial resins.

SUMMARY

The present invention thus relates to an electro-conductive embedding medium for a biological sample comprising:
- from 60% to 99% wt. of a glycol dimethacrylate selected from alkylene glycol dimethacrylate and/or oligo(alkylene glycol) dimethacrylate;
- a polyalkylene glycol diacrylate or of a polyalkylene glycol methacrylate; said polyalkylene glycol diacrylate or polyalkylene glycol methacrylate being optionally substituted by at least one hydrophilic group such as hydroxyl, amino, or an oxo group;
- at least one additive, preferably comprising at least one heavy metal salt or lanthanide salt; and
- a radical polymerization initiator.

According to one embodiment, the electro-conductive embedding medium for a biological sample comprises:
- from 60% to 99% wt. of a glycol dimethacrylate selected from alkylene glycol dimethacrylate and/or oligo(alkylene glycol) dimethacrylate;
- from 0% to 38% wt. of a polyalkylene glycol diacrylate or of a polyalkylene glycol methacrylate; said polyalkylene glycol diacrylate or polyalkylene glycol methacrylate being optionally substituted by at least one hydrophilic group such as hydroxyl, amino, or an oxo group; and
- from 0.1% to 2% wt. of a radical polymerization initiator.

According to one embodiment, the glycol dimethacrylate is selected from ethylene glycol dimethacrylate, diethylene glycol dimethacrylate, triethylene glycol dimethacrylate, propylene glycol dimethacrylate and butylene glycol dimethacrylate; preferably the glycol dimethacrylate is triethylene glycol dimethacrylate.

According to one embodiment, the polyalkylene glycol diacrylate is selected from polyethylene glycol diacrylate, polypropylene glycol diacrylate and polybutylene glycol diacrylate; preferably the polyalkylene glycol diacrylate is polypropylene glycol diacrylate.

According to one embodiment, the polyalkylene glycol methacrylate is selected from polyethylene glycol methacrylate, polypropylene glycol methacrylate and polybutylene glycol methacrylate; said polyalkylene glycol methacrylate being optionally substituted by at least one hydrophilic group such as hydroxyl, amino, or an oxo group; preferably the polyalkylene glycol methacrylate is hydroxyl polyethylene glycol methacrylate.

According to one embodiment, the radical polymerization initiator is a photoinitiator or a thermoinitiator, preferably the radical polymerization initiator is a photoinitiator, more preferably is benzoine methyl ether or 2-hydroxy-2-methyl-1-phenyl-propan-1-one.

According to one embodiment, the electro-conductive embedding medium comprises:
- from 60% to 99% wt. of triethylene glycol dimethacrylate;
- from more than 0% to 38% wt. of polypropylene glycol diacrylate; and
- from 0.1% to 2% wt. of a radical polymerization initiator.

According to one embodiment, the electro-conductive embedding medium comprises:
- from 60% to 99% wt. of triethylene glycol dimethacrylate:
- from more than 0% to 38% wt. of hydroxyl polyethylene glycol methacrylate; and
- from 0.1% to 2% wt. of a radical polymerization initiator.

According to one embodiment, the electro-conductive embedding medium comprises at least one heavy metal salt, more preferably comprising osmium and/or uranyl acetate.

According to one embodiment, the electro-conductive embedding medium further comprises at least one biological sample, preferably a vitrified and/or chemically fixed and/or dehydrated biological sample.

The present invention also relates to an electro-conductive imaging material comprising at least one biological sample embedded in a polymer matrix resulting from the polymerization of the embedding medium as defined above.

According to one embodiment, the electro-conductive material preserves the internal fluorescence, the protein activity and/or the antigenic specificity of the embedded biological sample.

The present invention also relates to a method for imaging by microscopy a biological sample comprising the following steps:
(i-1) fixing and/or dehydrating the biological sample;
(ii) infiltrating on the biological sample of step (i-1) an electro-conductive embedding medium as defined above;
(iii) polymerizing the mixture obtained at step (ii), resulting in an electro-conductive imaging material;
(iv) imaging by light microscopy and/or electron microscopy the electro-conductive imaging material of step (iii).

According to one embodiment, the method further comprises a step of microtomy or ultra-microtomy on the electro-conductive imaging material.

The present invention also relates to the use of an embedding medium as defined above, or of an electro-conductive imaging material as defined above, for imaging a biological sample by microscopy, preferably by light and/or electron microscopy.

The present invention also relates to a kit for preparing a biological sample to be imaged in microscopy, comprising:
a first container comprising (a) a glycol dimethacrylate selected from alkylene glycol dimethacrylate and/or oligo(alkylene glycol) dimethacrylate; and (b) a polyalkylene glycol diacrylate or a polyalkylene glycol methacrylate, said polyalkylene glycol diacrylate or polyalkylene glycol methacrylate being optionally substituted by at least one hydrophilic group such as hydroxyl, amino, or an oxo group;

a second container comprising radical polymerization initiator;

or comprising:

a container comprising (a) an glycol dimethacrylate selected from alkylene glycol dimethacrylate and/or oligo(alkylene glycol) dimethacrylate; (b) a polyalkylene glycol diacrylate or a polyalkylene glycol methacrylate, said polyalkylene glycol diacrylate or polyalkylene glycol methacrylate being optionally substituted by at least one hydrophilic group such as hydroxyl, amino, or an oxo group; and (c) a radical polymerization initiator;

and mixing means.

DETAILED DESCRIPTION

Figure 1:
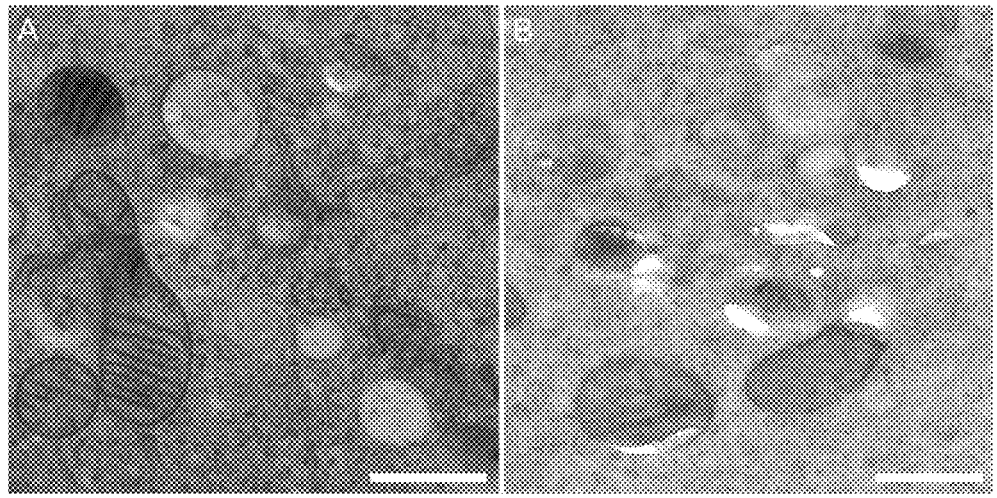
FIG. 1 is a cliché of HeLa cells embedded in the embedding medium of the invention (FIG. 1A), or in a Lowicryl® resin (FIG. 1B), obtained by transmission electron microscopy (TEM).

In the present invention, the following terms have the following meanings:

"About": preceding a figure means plus or less 10% of the value of said figure.

"Acrylate": refers to a vinyl monomer having at least one $CH_2=CH-COO$-group.

"Amino": refers to any compound derived from ammoniac $NH_3$ by substitution of one or more hydrogen atoms with an organic radical. Amino preferably refers to $-NH_2$, $-NHR$ and $-NRR'$ wherein R and R' are preferably alkyl groups. Therefore "amino" includes monoalkylamino and dialkylamino groups.

"Biological sample": refers to any biological material collected from animal or vegetal or living human body such as for example cell extract, cell, tissue or organ. Biological sample does not refer to implants.

"Embedding medium" refer to the medium in which a biological sample is placed so that the resulting material may be imaged by microscopy, directly or after being cut by using a microtome or an ultra-microtome. Embedding medium does not refer to objects or metals used as implants.

"Glycol": refer to any organic chemical compound having at least one diol group and for which each hydroxyl group is located on different carbon atoms. According to one embodiment, each hydroxyl group of the glycol compound is located at one end of said glycol compound. According to one embodiment, the glycol has at least one vicinal diol i.e. two hydroxyl groups attached to adjacent carbon atoms. Glycol compounds include alkylene glycol such as ethylene glycol, propylene glycol or butylene glycol; oligo(alkylene glycol) such as diethylene glycol, triethylene glycol or tetraethylene glycol; and polyalkylene glycol such as poly(ethylene glycol), poly(propylene glycol) or poly(butylene glycol) for example.

"Glycol acrylate": refers to any glycol compound for which one of the two hydroxyl functions of said glycol has been involved in a reaction with acrylic acid or acryloyl halide for providing a compound having both a hydroxyl function and an acrylate group. The terms "glycol acrylate" include alkylene glycol acrylate, oligo(alkylene glycol) acrylate and polyalkylene glycol acrylate.

"Glycol diacrylate": refers to any glycol compound for which the two hydroxyl functions of said glycol have been involved in a reaction with acrylic acid or acryloyl halide for providing a compound having two acrylate groups. The terms "glycol diacrylate" include alkylene glycol diacrylate, oligo(alkylene glycol) diacrylate and polyalkylene glycol diacrylate.

"Glycol dimethacrylate": refers to any glycol compound for which the two hydroxyl functions of said glycol have been involved in a reaction with methacrylic acid or methacryloyl halide for providing a compound having two methacrylate groups. The terms "glycol dimethacrylate" include alkylene glycol dimethacrylate, oligo(alkylene glycol) dimethacrylate and polyalkylene glycol dimethacrylate.

"Glycol methacrylate": refers to any glycol compound for which one of the two hydroxyl functions of said glycol has been involved in a reaction with methacrylic acid or methacryloyl halide for providing a compound having both a hydroxyl function and a methacrylate group. The terms "glycol methacrylate" include alkylene glycol methacrylate, oligo(alkylene glycol) methacrylate and polyalkylene glycol methacrylate.

"Heavy metal salt": refers to any salt comprising a heavy metal (i.e. metals with relatively high densities, atomic weights, or atomic numbers) According to one embodiment, the heavy metal is selected from iron, cobalt, zinc, ruthenium, silver, indium, cadmium, mercury, lead, uranium, osmium and copper.

"Hydrophilic": defines a molecule or a portion of a molecule that is typically charge-polarized and capable of hydrogen bonding, enabling it to dissolve more readily in water than in oil or other solvents.

"Hydroxyl": refers to the chemical function $-OH$.

"Initiator": refers to any chemical compound able to initiate a polymerization reaction, preferably a radical polymerization. In the present invention, the initiator provides radical entities able to react with first vinyl monomer units so that to initiate the growth of the polymer chains.

"Lowicryl®": refers to a commercially available embedded medium based on an acrylate and/or methacrylate resin. Lowicryl® HM 20 refers to a non-polar embedded medium comprising or being constituted by 2-propenoic acid-2-methyl-1,2-ethanediylbis(oxy-2,1-ethanediyl)ester (CAS 106-16-0); 2-Propenoic acid-2-methyl ethyl ester (CAS 97-63-2); n-Hexyl methacrylate and optionally 4-Methoxyphenol and/or acetophenone-2-methoxy-2-phenyl (CAS 3524-62-7). According to one embodiment, the term "Lowicryl" includes the commercially available products Lowicryl® HM 20, Lowicryl® HM 21 and Lowicryl® HM 23.

"Macromonomer": refers to a polymer chain having at least one end group able to act as a monomer. According to one embodiment, the term "Matrix": refers to a chemical network, preferably an organic chemical network, more preferably an organic polymer network. According to one embodiment, the network is a covalently crosslinked "Imaging material": refers to a solid or a semi-solid embedding a biological sample and suitable for being used in an analysis by microscopy.

"Methacrylate": refers to a vinyl monomer having at least one $CH_2=C(CH_3)$—COO— group.

"Microscopy": refers to the general field encompassing techniques for imaging an object using microscopes.

"Microtomy": refers to the method for preparing an object for its microscopy study, said method comprising using a microtome or ultra-microtome (i.e. an apparatus suitable for slicing thinly the sample to be analyzed by microscopy). According to one embodiment, the term "microtomy" encompasses focused ion beam milling technologies.

"Electron microscopy": refers to a microscope using a beam of accelerated electrons as a source of illumination of a sample and providing an enlarged image.

"Light microscopy": refers to a microscope using a beam of photons of controlled wavelength as a source of illumination of a sample and providing an enlarged image.

"Electro-conductive": refers to any material or compound able to conduct electrons. According to one embodiment, the term "electro-conductive" refers to a material or a compound able to evacuate the electrons accumulated on its surface.

"Freeze Substitution": refers to a process of dehydration of a biological sample, performed at temperatures low enough to avoid the formation of ice crystals and avoiding the damaging effects observed after ambient-temperature dehydration of the same sample. In the present invention, the Freeze Substitution process refers to a process in which first, the frozen water of the sample is dissolved by an organic solvent, optionally comprising chemical fixatives; then, the sample is embedded in a resin; and finally the sample is progressively warmed up for its imaging by microscopy.

"High Pressure Freezing": refers to a cryofixation method of a biological sample under high pressure, preferably at a pressure ranging from 2000 bars to 2700 bars, more preferably at a pressure of about 2048 bars.

"Oxo": refers to the chemical function —C(O)—.

"Polymer": refers to a macromolecular compound consisting of repeating units (the monomers). According to one embodiment, the term "polymer" refers to an organic macromolecular compound consisting of repeating units.

"Photoinitiator": refers to any chemical compound able to initiate a polymerization reaction, preferably a radical polymerization, when exposed to radiation (UV or visible). In the present invention, the photoinitiator when exposed to radiation, provides radical entities able to react with first vinyl monomer units so that to initiate the growth of the polymer chains.

"Radical polymerization" refers to any polymerization reaction techniques in which the growth of the polymer chain is implemented by successive additions of free radical monomers. In the present invention, the expression "radical polymerization" refers to a process for providing a polymer comprising the three following steps: (1) initiation, (2) propagation and (3) termination, well-known by the skilled artisan.

"Thermo-initiator": refers to any chemical compound able to initiate a polymerization reaction, preferably a radical polymerization, when exposed to heat. In the present invention, the thermo-initiator when exposed to heat, provides radical entities able to react with first vinyl monomer units so that to initiate the growth of the polymer chains.

"Ultra-Microtomy": refers to the method for preparing an object for its microscopy study, said method comprising using an ultra-microtome (i.e. an apparatus fitted with either a diamond knife or a glass knife, suitable for ultra-thinly slicing the sample to be analyzed by microscopy).

"Vitrification": refers to a process by which a biological material is transformed into a solid containing amorphous water in which all cellular components are kept in a close-to-life state. In the present invention, the expression "vitrified biological sample" refers to the biological sample obtained after a vitrification.

Embedding Medium

This invention relates to an embedding medium, preferably an embedding medium for a biological sample, even more preferably an embedding medium for infiltrating and impregnating a biological sample. According to one embodiment, the invention relates to an embedding medium for imaging a biological sample, preferably by microscopy, more preferably by electron microscopy. According to one embodiment, the embedding medium is electro-conductive.

According to one embodiment, the embedding medium is a composition comprising or being constituted of organic compounds.

According to one embodiment, the embedding medium comprises or is constituted of a polymer precursor formulation. According to one embodiment, the embedding medium comprises or is constituted of a monomer mixture and optionally an initiator.

According to one embodiment, the embedding medium comprises or is constituted of a monomer mixture wherein at least one monomer has formula (I):

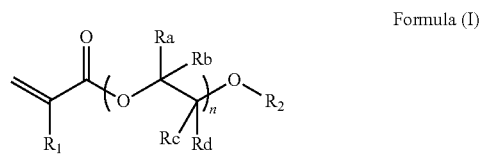

Formula (I)

wherein:
R$_1$ represents H, linear or branched alkyl, preferably R$_1$ represents H or methyl;
R$_2$ represents H, methacryloyl, acryloyl, linear or branched alkyl, preferably R$_1$ represents H, a methacryloyl or acryloyl group;
R$_a$, R$_b$, R$_c$, and R$_d$ are each independently selected from H, linear or branched alkyl, preferably from H or methyl; and
n is a positive integer.

According to one embodiment, the embedding medium comprises or is constituted of a monomer mixture comprising:
a monomer of formula (II-A):

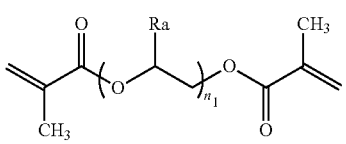

Formula (II-A)

a monomer of formula (II-B):

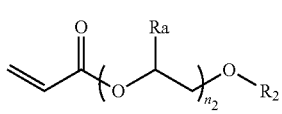

Formula (II-B)

and/or
a monomer of formula (II-C):

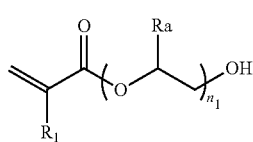

Formula (II-C)

wherein:
R$_1$ represents H, linear or branched alkyl, preferably R$_1$ represents H or methyl;
R$_2$ represents H, methacryloyl, acryloyl, linear or branched alkyl, preferably R$_1$ represents H, a methacryloyl or acryloyl group;
R$_a$ represents H, linear or branched alkyl: preferably from H or methyl; and
n$_1$ is a positive integer ranging from 1 to 5, preferably 3;
n$_2$ and n$_3$ represent each independently a positive integer higher than 5, preferably ranging from 10 to 100, more preferably ranging from 10 to 40.

According to one embodiment, the monomer mixture comprises or is constituted of at least one monomer, preferably of at least one radically polymerizable monomer, more preferably of at least one hydrophilic radically polymerizable monomer. According to one embodiment, the monomer mixture comprises or is constituted of at least one hydrophilic monomer. According to one embodiment, the monomer mixture comprises or is constituted of a mixture of two radically polymerizable monomers.

According to one embodiment, the radically polymerizable monomer is selected from the group of acrylates, methacrylates, diacrylates and/or dimethacrylates, said group being optionally substituted by at least one hydrophilic group such as hydroxyl, amino, or an oxo group.

According to one embodiment, the embedding medium comprises:
a polyalkylene glycol (di)acrylate and/or a polyalkylene glycol (di)methacrylate, said polyalkylene glycol diacrylate or polyalkylene glycol methacrylate being optionally substituted by at least one hydrophilic group such as hydroxyl, amino, or an oxo group; and
an initiator.

According to one embodiment, the embedding medium comprises:
an alkylene glycol dimethacrylate;
a polyalkylene glycol diacrylate or a polyalkylene glycol methacrylate, said polyalkylene glycol diacrylate or polyalkylene glycol methacrylate being optionally substituted by at least one hydrophilic group such as hydroxyl, amino, or an oxo group; and
an initiator.

According to one embodiment, embedding medium does not comprise dimethylaminoethyl methacrylate (DEMA), hydroxyethyl methacrylate (HEMA), polymethylmethacrylate (PMMA), poly(lactic-co-glycolic acid) (PLGA), polylactic acid (PLA) or polyethylene glycol (PEG).

According to one embodiment, the monomer mixture comprises or is constituted of one diacrylate and one dimethacrylate, preferably of one glycol diacrylate and one glycol dimethacrylate; said glycol diacrylate and/or glycol dimethacrylate being optionally substituted by at least one hydrophilic group such as hydroxyl, amino, or an oxo group.

According to one embodiment, the monomer mixture comprises or is constituted of one alkylene glycol dimethacrylate and one polyalkylene glycol diacrylate, said alkylene glycol dimethacrylate and/or polyalkylene glycol diacrylate being optionally substituted by at least one hydrophilic group such as hydroxyl, amino, or an oxo group.

According to one embodiment, the monomer mixture comprises or is constituted of one alkylene glycol dimethacrylate and one polyalkylene glycol methacrylate, said alkylene glycol dimethacrylate and/or polyalkylene glycol methacrylate being optionally substituted by at least one hydrophilic group such as hydroxyl, amino, or an oxo group.

According to one embodiment, the alkylene glycol dimethacrylate is selected from ethylene glycol dimethacrylate, propylene glycol dimethacrylate and butylene glycol dimethacrylate; preferably the alkylene glycol dimethacrylate is ethylene glycol dimethacrylate.

According to one embodiment, the polyalkylene glycol diacrylate is selected from polyethylene glycol diacrylate, polypropylene glycol diacrylate and polybutylene glycol diacrylate; preferably the polyalkylene glycol diacrylate ispolypropylene glycol diacrylate.

According to one embodiment, the polyalkylene glycol methacrylate is selected from polyethylene glycol methacrylate, polypropylene glycol methacrylate and polybutylene glycol methacrylate, said polyalkylene glycol methacrylate being optionally substituted by at least one hydrophilic group such as hydroxyl, amino, or an oxo group; preferably the polyalkylene glycol methacrylate is hydroxyl polyethylene glycol methacrylate.

According to one embodiment, the monomer mixture comprises or is constituted of triethylene glycol dimethacrylate (TGdMA) and polypropylene glycol diacrylate (PPGdA). According to one embodiment, the embedding medium comprises or is constituted of triethylene glycol dimethacrylate, polypropylene glycol diacrylate and an initiator.

According to one embodiment, the initiator is a radical polymerization initiator. According to one embodiment, the initiator is a photoinitiator. According to one embodiment, the initiator is a thermoinitiator.

According to one embodiment, the photoinitiator is selected from 2-tert-butylanthraquinone, camphorquinone, diphenyl(2,4,6-trimethylbenzoyl)phosphine oxide, 9,10-phenanthrenequinone, phenylbis(2,4,6-trimethylbenzoyl) phosphine oxide, 2-benzyl-2-(dimethylamino)-4'-morpholinobutyrophenone, 3,6-bis(2-methyl-2-morpholinopropionyl)-9-octylcarbazole, 4'-tert-butyl-2',6'-dimethylacetophenone, 2,2-diethoxyacetophenone, 4'-ethoxyacetophenone, 3'-hydroxyacetophenone, 4'-hydroxyacetophenone, 1-hydroxycyclohexylphenylcetone, 2-hydroxy-4'-(2-hydroxyethoxy)-2-methylpropiophenone, 2-hydroxy-2-methylpropiophenone, 2-methyl-4'-(methylthio)-2-morpholinopropiophenone, 4'-phenoxyacetophenone, benzoin, benzoinethyl ether, benzoinmethyl ether, 4,4'-dimethylbenzoin, 4,4'-dimethylbenzile, benzophenone, benzoyl biphenyl, 4,4'-bis(diethylamino)benzophenone, 4,4'-dihydroxybenzophenone, 3,4-dimethylbenzophenone, 3-hydroxybenzophenone, 4-hydroxybenzophenone, 2-methylbenzophenone, 3-methylbenzophenone, 4-methylbenzophenone, methyl benzoylformate, Michler's ketone, 1-chloro-4-propoxy-9H-thioxanthen-9-one, 2-chlorothioxanthen-9-one, 2,4-diethyl-9H-thioxanthen-9-one, isopropyl-9H-thioxanthen-9-one, 10-methylphenothiazine, thioxanthen-9-one, diaryliodonium hexafluorophosphate salt, diaryliodonium hexafluoroantimonate salt, triarylsulfonium hexafluorophosphate salt, hexafluorophosphate, and triarylsulfonium hexafluoroantimonate salt.

According to one embodiment, the thermo-initiator is selected from azo compounds such as 2,2'-azobis(isobutyronitrile) (AIBN), 4,4'-azobis-(4-cyanovaleric acid), 1,1'-azobis(cyclohexanecarbonitrile), 2,2'-azobis(2-methylpropionamidine)dihydrochloride, 2,2'-azobis(2-methylpropionitrile); and organic peroxides such as benzoyl peroxide (BPO).

According to one embodiment, the alkylene glycol dimethacrylate or any derivatives thereof, ranges from 60% to 99% wt., preferably from 65% to 99%, from 70% to 99%, from 75% to 99%, from 80% to 99%, from 85% to 99%, from 90% to 99% in weight to the total weight of the embedding medium. According to one embodiment, the alkylene glycol dimethacrylate ranges from 60% to 99% wt., preferably from 60% to 90%, from 60% to 85%, from 60% to 80%, from 60% to 75%, from 60% to 70%, in weight to the total weight of the embedding medium. According to one embodiment, the alkylene glycol dimethacrylate is about 60, 61, 62, 63, 64, 65, 66, 67, 6, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99%, in weight to the total weight of the embedding medium. According to one embodiment, alkylene glycol dimethacrylate or any derivatives thereof ranges from 70% to 90%, from 75% to 85%, more preferably is 80%, in weight to the total weight of the embedding medium.

According to one embodiment, the alkylene glycol dimethacrylate or any derivatives thereof, ranges from 0.1% to 100%; preferably from 0.1% to 90%; from 1% to 90%; from 10% to 90%; from 15% to 90%; from 20% to 90%; from 25% to 90%; from 30% to 90%; from 35% to 90%; from 40% to 90%; from 45% to 90%; from 50% to 90%; from 55% to 90%; from 60% to 90%; from 65% to 90%; from 70% to 90%; from 75% to 90%; from 80% to 90%; or from 85% to 90%, in weight to the total weight of the embedding medium. According to one embodiment, the alkylene glycol dimethacrylate ranges from 0.1% to 99%; preferably from 0.1% to 95%, from 0.1% to 90%, from 0.1% to 85%, from 0.1% to 80%, from 0.1% to 75%, from 0.1% to 70%, from 0.1% to 65%, from 0.1% to 60%, from 0.1% to 55%, from 0.1% to 50%, from 0.1% to 45%, from 0.1% to 40%, from 0.1% to 35%, from 0.1% to 30%, from 0.1% to 25%, from 0.1% to 20%, from 0.1% to 15%, from 0.1% to 10%, or from 0.1% to 5%, in weight to the total weight of the embedding medium.

According to one embodiment, the polyalkylene glycol diacrylate or any derivatives thereof, ranges from more than 0% to 38% wt., preferably from 1% to 38%, from 5% to 38%, from 10% to 38%, from 15% to 38%, from 20% to 38%, from 25% to 38%, from 30% to 38%, in weight to the total weight of the embedding medium. According to one embodiment, the polyalkylene glycol diacrylate or any derivatives thereof, ranges from more than 0% to 38% wt., preferably from 1% to 35%, from 1% to 30%, from 1% to 25%, from 1% to 20%, from 1% to 15%, from 1% to 10%, from 1% to 5%, in weight to the total weight of the embedding medium.

According to one embodiment, the polyalkylene glycol diacrylate any derivatives thereof, ranges from more than 0% to 50%, preferably from 0.1% to 50%, from 5% to 50%, from 10% to 50%, from 15% to 50%, from 20% to 50%, from 25% to 50%, from 30% to 50%, from 35% to 50%, from 40% to 50%, or from 45% to 50%, in weight to the total weight of the embedding medium. According to one embodiment, the polyalkylene glycol diacrylate ranges from more than 0% to 50%, preferably from 0.1% to 45%, from 0.1% to 40%, from 0.1% to 35%, from 0.1% to 30%, from 0.1% to 25%, from 0.1% to 20%, from 0.1% to 15%, from 0.1% to 10%, or from 0.1% to 5%, in weight to the total weight of the embedding medium. According to one embodiment, the polyalkylene glycol diacrylate ranges from more than 0% to 50%, preferably from 1% to 40%, from 5% to 30%, more preferably from 10% to 25%, more preferably is 20%, in weight to the total weight of the embedding medium.

According to one embodiment, the polyalkylene glycol methacrylate or any derivatives thereof, ranges from more than 0% to 38% wt., preferably from 1% to 38%, from 5% to 38%, from 10% to 38%, from 15% to 38%, from 20% to 38%, from 25% to 38%, from 30% to 38%, in weight to the total weight of the embedding medium. According to one embodiment, the polyalkylene glycol methacrylate or any derivatives thereof, ranges from more than 0% to 38% wt., preferably from 1% to 35%, from 1% to 30%, from 1% to 25%, from 1% to 20%, from 1% to 15%, from 1% to 10%, from 1% to 5%, in weight to the total weight of the embedding medium.

According to one embodiment, the alkylene glycol diacrylate or any derivatives thereof, have a molar weight ranging from 100 to 500 kDa; preferably from 100 to 400 kDa, from 100 to 300 kDa, from 100 to 200 kDa. According to one embodiment, the molar weight of alkylene glycol diacrylate or any derivatives thereof, is about 150 kDa, preferably is 150 kDa. According to one embodiment, the molar weight of triethylene glycol dimethacrylate (TGdMA) is about 150 kDa, preferably is 150 kDa.

According to one embodiment, the polyalkylene glycol diacrylate or any derivatives thereof, have a molar weight ranging from 500 to 1500 kDa, preferably from 500 to 100 kDa, from 700 to 900 kDa, from 750 to 850 kDa. According to one embodiment, the polyalkylene glycol diacrylate or any derivatives thereof, have a molar weight about 800 kDa. According to one embodiment, the molar weight of polyalkylene glycol diacrylate or any derivatives thereof is 800 kDa. According to one embodiment, the molar weight of polypropylene glycol diacrylate is about 800 kDa, preferably is 800 kDa.

According to one embodiment, the embedding medium comprises or is constituted of:
- 79% wt. of one alkylene glycol dimethacrylate, preferably triethylene glycol dimethacrylate;
- 20% wt. of one polyalkylene glycol diacrylate, preferably polypropylene glycol diacrylate; and
- 1% wt. of a radical polymerizable initiator, preferably a radical polymerizable photoinitiator, more preferably benzoin methyl ether.

According to one embodiment, the embedding medium comprises:
- from 60% to 99% wt. of triethylene glycol dimethacrylate;
- from more than 0% to 38% wt. of polypropylene glycol diacrylate; and
- from 0.1% to 2% wt. of a radical polymerization initiator; preferably benzoin methyl ether.

According to one embodiment, the embedding medium comprises:
- from 98% to 99.9% wt. of triethylene glycol dimethacrylate; and
- from 0.1% to 2% wt. of a radical polymerization initiator; preferably benzoin methyl ether.

According to one embodiment, the embedding medium comprises:
- from 60% to 99% wt. of triethylene glycol dimethacrylate;
- from more than 0% to 38% wt. of hydroxyl polyethylene glycol methacrylate; and
- from 0.1% to 2% wt. of a radical polymerization initiator: preferably benzoin methyl ether.

According to one embodiment, the embedding medium further comprises a solvent, preferably a volatile solvent, more preferably an alcohol such as ethanol. According to one embodiment, the embedding medium further comprises acetone.

According to one embodiment, the embedding medium further comprises at least one additive selected from contrasting agents, and/or compounds useful for freeze substitution such as fixative agents and/or solvents, preferably comprising at least one heavy metal salt, more preferably comprising silver nitrate, osmium and/or uranyl acetate. According to one embodiment, the embedding medium further comprises at least one additive ranging from more than 0% to 5% by weight to the total weight of embedding medium. According to one embodiment, the embedding medium comprises 0.5% by weight to the total weight of embedding medium. According to one embodiment, the embedding medium comprises 0.01% by weight to the total weight of embedding medium. According to one embodiment, the compounds useful for freeze substitution is selected from acetone, anhydrous acetone, uranyl acetate, tannic acid, aldehyde such as glutaraldehyde or paraformaldehyde; and any combinations thereof. According to one embodiment, the fixative agent is selected from osmium, osmium tetroxide, uranyl acetate, glutaraldehyde, paraformaldehyde, or any combinations thereof. According to one embodiment, the contrasting agent is selected from uranyl acetate, lead derivatives, silver derivatives, osmium derivatives, lanthanide salts, polyphenols preferably polyphenols contained in tannins, gallic acid and tannic acid.

According to one embodiment, the embedding medium further comprises hydrophilic compounds.

According to one embodiment, the embedding medium further comprises at least one biological sample, preferably a vitrified biological sample and/or chemically fixed biological sample and/or a dehydrated biological sample. According to one embodiment, the biological sample is a cell extract. According to one embodiment, the biological sample is a cell. According to one embodiment, the biological sample is a tissue. According to one embodiment, the biological sample is an organ. According to one embodiment, the biological sample is a HeLa cell. According to one embodiment, the biological sample is melanocyte.

According to one embodiment, the embedding medium is liquid. According to one embodiment, the embedding medium is semi-solid. According to one embodiment, the embedding medium is polymerizable at low temperatures, preferably at temperature below 0° C., preferably at a temperature ranging from −90° C. to −10° C., more preferably at a temperature ranging from −40° C. to −20° C. According to one embodiment, the embedding medium is polymerizable at a temperature ranging from −70° C. to −20° C., preferably at −35° C., at −40° C. or at −45° C. According to one embodiment, the embedding medium is polymerizable at a temperature ranging from −90° C. to −10° C., preferably from −80° C. to −10° C., from −70° C. to −10° C., from −70° C. to −10° C., from −60° C. to −10° C., from −50° C. to −10° C., from −40° C. to −10° C., from −30° C. to −10° C., or from −20° C. to −10° C. According to one embodiment, the embedding medium is polymerizable at a temperature ranging from −90° C. to −10° C., preferably from −90° C. to −20° C., from −90° C. to −30° C. from −90° C. to −40° C., from −90° C. to −50° C., from −90° C. to −60° C., from −90° C. to −70° C., or from −90° C. to −80° C.

According to one embodiment, the embedding medium is not or does not comprise a Lowicryl® resin. According to one embodiment, the embedding medium does not comprise phenol or its derivatives. According to one embodiment, the embedding medium does not comprise methoxyphenol. According to one embodiment, the embedding medium does not comprise alkyl methacrylate. According to one embodiment, the embedding medium does not comprise hexyl methacrylate. According to one embodiment, the embedding medium does not comprise bisphenol A or its derivatives. According to one embodiment, the embedding medium does not comprise ethoxylated bisphenol A dimethacrylate.

Imaging Material

The invention also relates to a supporting material for microscopy. According to one embodiment, the supporting material is a material for its use in microscopy, preferably as an embedding material for a sample to be imaged (called "imaging material"). According to one embodiment, the imaging material of the invention results from the polymerization of the embedding medium as defined above.

According to one embodiment, the imaging material of the invention is electro-conductive. According to one embodiment, the imaging material does not accumulate any electrons on its surface during a microscopy analysis. According to one embodiment, the imaging material of the invention is antistatic.

According to one embodiment, the imaging material of the invention is transparent. According to one embodiment, the imaging material of the invention is a semi-solid or a solid. According to one embodiment, the imaging material of the invention comprises or is constituted of a cross-linked polymer matrix and optionally at least one biological sample. According to one embodiment, the imaging material of the invention preserves the physical properties of the embedded biological sample such as its fluorescence and/or the preservation of its proteins ultrastructures. According to one embodiment, the imaging material of the invention preserves proteins ultrastructures of the embedded biological sample so that the detection of the antibodies for immunodetection is imagable by microscopy.

According to one embodiment, the imaging material comprises at least one biological sample embedded in a polymer matrix resulting from the polymerization of the embedding medium as defined above.

According to one embodiment, the imaging material does not comprise epoxy resin. According to one embodiment, the imaging material does not comprise epoxide group. According to one embodiment, the imaging material does not comprise polyarylene ether.

Process for Manufacturing an Embedding Medium

The invention also relates to a process for manufacturing the embedding medium as defined above.

According to one embodiment, the process comprises or is constituted by mixing:
  at least one monomer as defined above, preferably at least one radically polymerizable monomer, more preferably at least one hydrophilic radically polymerizable monomer; and
  an initiator as defined above.

According to one embodiment, the process comprises or is constituted by mixing:
  two monomers as defined above, preferably two radically polymerizable monomers, more preferably two hydrophilic radically polymerizable monomers, in order to obtain a monomer mixture; and
  optionally an initiator as defined above.

According to one embodiment, the process comprises or is constituted by mixing:
  an alkylene glycol dimethacrylate;
  a polyalkylene glycol diacrylate or a polyalkylene glycol methacrylate, said polyalkylene glycol diacrylate or polyalkylene glycol methacrylate being optionally substituted by at least one hydrophilic group such as hydroxyl, amino, or an oxo group; and
  an initiator as defined above.

According to one embodiment, the process further comprises adding a biological sample such as a cell extract, a cell, a tissue and/or an organ; preferably adding a vitrified biological sample and/or a dehydrated biological sample. According to one embodiment, the process further comprises adding additives such as heavy metal salts. According to one embodiment, the process further comprises adding silver nitrate and/or uranyl acetate.

According to one embodiment, the process for preparing the embedding medium is carried out at a temperature ranging from 0° C. to 40° C.; preferably from 5° C. to 30° C., from 10° C. to 30° C., from 15° C. to 30° C., from 20° C. to 30° C., from 25° C. to 30° C.: more preferably the process for preparing the embedding medium is carried out at a temperature of about 25° C.

Process for Manufacturing the Imaging Material

The invention also relates to a process for manufacturing the imaging material as defined above.

According to one embodiment, the process comprises:
  (a) providing an embedding medium as defined above; and
  (c) polymerizing the embedding medium.

According to one embodiment, the process further comprises infiltrating the embedding medium on a biological sample. According to one embodiment, the process comprises:
  (a) providing an embedding medium as defined above;
  (b) infiltrating the embedding medium on a biological sample in order to provide an embedded biological sample; and
  (c) polymerizing the embedded biological sample of step (b).

According to one embodiment, the process further comprises vitrifying a biological sample. According to one embodiment, the process comprises:
  (a-0) vitrifying a biological sample to obtain a vitrified biological sample;
  (a) providing an embedding medium as defined above;
  (b) infiltrating the embedding medium on the vitrified biological sample of step (a-0) in order to provide an embedded biological sample; and
  (c) polymerizing the embedded biological sample of step (b).

According to one embodiment, the process further comprises fixing and dehydrating the vitrified biological sample of step (a-0). According to one embodiment, the process comprises:
  (a-0) vitrifying a biological sample to obtain a vitrified biological sample;
  (a-1) fixing and dehydrating the vitrified biological sample of step (a-0);
  (a) providing an embedding medium as defined above;
  (b) infiltrating the embedding medium on the biological sample of step (a-1) in order to provide an embedded biological sample; and
  (c) polymerizing the embedded biological sample of step (b).

According to another embodiment, the process further comprises fixing and dehydrating the biological sample. According to one embodiment, the process comprises:
  (a-1) fixing and dehydrating the biological sample;
  (a) providing an embedding medium as defined above;
  (b) infiltrating the embedding medium on the biological sample of step (a-1) in order to provide an embedded biological sample; and
  (c) polymerizing the embedded biological sample of step (b).

According to one embodiment, the step (a-0) is carried out by a cryogenic method well-known by the skilled artisan, preferably by High Pressure Freezing process.

According to one embodiment, the step (a-1) is carried out by any method well-known by the skilled artisan, preferably by a Freeze Substitution process. According to one embodiment, the step (a-1) is carried out by using at least one fixative agent, preferably selected from osmium, osmium tetroxide, uranyl acetate, paraformaldehyde, and aldehydes such as glutaraldehyde, or any combinations thereof. According to one embodiment, the step (a-1) is carried out by using at least one contrasting agent, preferably selected from heavy metal salts. According to one embodiment, the step (a-1) is carried out by using at least one contrasting agent, preferably selected from lanthanide salts. According to one embodiment, the contrasting agent is selected from uranyl acetate, lead derivatives, silver derivatives, osmium derivatives, lanthanide salts, polyphenols preferably polyphenols contained in tannins, gallic acid and tannic acid. According to one embodiment, the step (a-1) is carried out at a temperature ranging from −90° C. to −30° C. According to one embodiment, the step (a-1) is carried out at a temperature ranging from −70° C. to −20° C., preferably at −35° C., at −40° C. or at −45° C. According to one embodiment, the step (a-1) is carried out at a temperature ranging from −90° C. to −30° C. preferably from −80° C. to −40° C., or from −60° C. to −50° C.

According to one embodiment, the step (a) is carried out according to the process for preparing the embedding medium as defined above.

According to one embodiment, the polymerization is carried out at a temperature ranging from −90° C. to −10° C., preferably at a temperature ranging from −40° C. to −20° C. According to one embodiment, the polymerization is carried out at a temperature ranging from −70° C. to −20° C., preferably at −35° C., at −40° C. or at −45° C. According to one embodiment, the polymerization is carried out at a temperature ranging from −90° C. to −10° C., preferably from −80° C. to −10° C., from −70° C. to −10° C., from −70° C. to −10° C., from −60° C. to −10° C., from −50° C. to −10° C. from −40° C. to −10° C. from −30° C. to −10° C. or from −20° C. to −10° C.

According to one embodiment, the polymerization is carried out at a temperature ranging from −90° C. to −10° C., preferably from −90° C. to −20° C., from −90° C. to −30° C., from −90° C. to −40° C., from −90° C. to −50° C., from −90° C. to −60° C. from −90° C. to −70° C., or from −90° C. to −80° C.

According to one embodiment, the polymerization is initiated by heat and/or by irradiation, preferably by UV or visible irradiation.

According to one embodiment, the contrasting agent ranges from 0.005 to 0.1%, preferably from 0.005 to 0.05%, from 0.005 to 0.015 in weight to the total weight of the imaging material. According to one embodiment, the contrasting agent is about 0.01% in weight to the total weight of the imaging material. According to one embodiment, the contrasting agent is 0.01% in weight to the total weight of the imaging material.

Method for Imaging a Biological Sample by (Electron) Microscopy

The invention also relates to a method for imaging a biological sample by microscopy, preferably by light and/or electron microscopy.

According to one embodiment, the method of the invention comprises or is constituted of the following steps:
providing an imaging material as defined above, preferably by the process for manufacturing the imaging material as defined above; and
imaging the imaging material, preferably by microscopy, more preferably by light microscopy and/or electron microscopy.

According to one embodiment, the method of the invention comprises or is constituted of the following steps:
(i-0) vitrifying a biological sample, preferably implemented by High Pressure Freezing process, plunge freezing, jet freezing and/or slam freezing;
(ii) infiltrating on the vitrified biological sample of step (i-0) an embedding medium as defined above, preferably by using a freeze substitution protocol;
(iii) polymerizing the mixture obtained at step (ii), resulting in an electro-conductive imaging material;
(iv) imaging by light microscopy and/or electron microscopy the electro-conductive imaging material of step (iii).

According to one embodiment, the method of the invention comprises or is constituted of the following steps:
(ii) infiltrating on the biological sample an embedding medium as defined above, preferably by using a freeze substitution protocol;
(iii) polymerizing the mixture obtained at step (ii), resulting in an electro-conductive imaging material;
(iv) imaging by light microscopy and/or electron microscopy the electro-conductive imaging material of step (iii).

According to one embodiment, the method further comprises a step of microtomy or ultra-microtomy on the electro-conductive imaging material.

According to one embodiment, the method further comprises a step of fixing and/or dehydrating the biological sample (step i-1), preferably after step (i-0). According to one embodiment, the method further comprises a step of fixing and/or dehydrating the vitrified biological sample (step i-1), preferably after step (i-0). According to one embodiment, the step (i-1) comprises using solvents, preferably acetone and/or ethanol; said solvents containing fixative agents and/or contrasting agents. According to one embodiment, the step (i-1) is carried out at a temperature ranging from −90° C. to −30° C.

According to one embodiment, the step (iv) is implemented by microscopy; preferably light microscopy, optical microscopy, fluorescent microscopy and/or electron microscopy; more preferably by electron microscopy. According to one embodiment, the step (iv) is implemented by correlative microscopy. According to one embodiment, the step (iv) is implemented by scanning electron microscopy (SEM). According to one embodiment, the step (iv) is implemented by transmission electron microscopy (TEM).

According to one embodiment, the step (iv) is implemented by correlative light and electron microscopy (CLEM). According to one embodiment, the step (iv) is implemented by epifluorescence, confocal, super-resolution or structured illuminated microscopy (SIM).

Uses

The invention also relates to the use of the embedding medium or the imaging material as defined above in microscopy, preferably in optical microscopy, fluorescent microscopy and/or electron microscopy; more preferably in electron microscopy. According to one embodiment, the embedding medium or the imaging material as defined above, is useful in correlative microscopy.

According to one embodiment, the embedding medium and/or the imaging material as defined above is (are) useful for imaging a biological sample such as a cell extract, a cell, a tissue and/or an organ; preferably for imaging a vitrified biological sample.

According to one embodiment, the embedding medium and/or the imaging material as defined above is (are) useful for specifically targeting cell structures and/or melanin. According to one embodiment, the embedding medium and/or the imaging material as defined above and comprising silver salts such as silver nitrate, is (are) useful for specifically targeting cell structures, preferably for specifically targeting cell structures labeled using gold coupled antibodies and/or melanin. According to one embodiment, the embedding medium and/or the imaging material as defined above and comprising silver salts such as silver nitrate, is (are) useful for specifically targeting cell structures and/or melanin at low temperature, preferably at a temperature below 0° C., more preferably ranging from −90° C. to −10° C.

According to one embodiment, the embedding medium and/or the imaging material as defined above is (are) useful for specifically targeting antibodies, preferably antibodies coupled to nano-sized gold nanoparticles. According to one embodiment, the embedding medium and/or the imaging material as defined above is (are) useful for specifically targeting antibodies coupled to nano-sized gold nanoparticles by aggregating silver nitrated encompassed in said embedding medium and/or imaging material. According to one embodiment, the embedding medium and/or the imaging material as defined above is (are) useful for generating silver enhancement reaction at low temperatures, preferably at a temperature below 0° C.

Kit

The invention also relates to a kit for preparing a biological sample to be imaged, preferably by microscopy.

According to one embodiment, the kit comprises a first container comprising at least one monomer as defined above; and a second container comprising an initiator. According to one embodiment, the kit comprises a first container comprising a hydrophilic monomer mixture as defined above; and a second container comprising an initiator.

According to one embodiment, the kit comprises:
- a first container comprising (a) an alkylene glycol dimethacrylate and (b) a polyalkylene glycol diacrylate or a polyalkylene glycol methacrylate, said polyalkylene glycol diacrylate or polyalkylene glycol methacrylate being optionally substituted by at least one hydrophilic group such as hydroxyl, amino, or an oxo group;
- a second container comprising radical polymerization initiator.

According to one embodiment, the kit comprises:
- a first container comprising (a) triethylene glycol dimethacrylate and (b); poly(propylene glycol) diacrylate; and
- a second container comprising benzoin methyl ether or hydroxyl-2-methylpropriophenone.

According to one embodiment, the present invention also refers to a kit comprising a container comprising at least one monomer and an initiator as defined above; and mixing means.

According to one embodiment, the present invention also refers to a kit comprising:
- a container comprising (a) an alkylene glycol dimethacrylate, (b) a polyalkylene glycol diacrylate or a polyalkylene glycol methacrylate, said polyalkylene glycol diacrylate or polyalkylene glycol methacrylate being optionally substituted by at least one hydrophilic group such as hydroxyl, amino, or an oxo group; and (c) a radical polymerization initiator; and
- mixing means.

According to one embodiment, the mixing means are for example but not limited to: containers, capsules, mixers, and/or spatulas.

ABBREVIATIONS

° C.: Celsius degree
CDCl$_3$: deuterated chloroform
CLEM: correlative light and electron microscopy
Eq.: equivalent
PEG: polyethylene glycol
PPGdA: poly(propylene glycol) diacrylate
g: gram(s)
h: hour(s)
mmol: millimole(s)
mol: mole(s)
NMR: Nuclear Resonance Magnetic
TGdMA: triethylene glycol dimethacrylate
UV: Ultraviolet Materials and Methods Reagents, solvents and starting materials were purchased from Sigma Aldrich and used without further purification.

UV Irradiation

The UV irradiation of the samples is carried out by using UV lamp system F300S Heraeus Noblelight® from Fusion UV, or an AFS-1 or AFS-2 from Leica for Freeze Substitution protocol (Automated Freeze Substitution automate).

Part I—Preparation of the Embedding Medium

Example 1: Synthesis of Poly(Propylene Glycol) Diacrylate (PPGdA)

PPGdA was synthetized by acryloylation: poly(propylene glycol) of 800 g/mol (20 g, 25 mmol) and triethylamine (11.7 g, 115 mmol), were introduced in a round bottom flask with 140 mL of dichloromethane. The mixture was cooled down to 5° C. and acryloyl chloride (9.5 g, 105 mmol) was added dropwise under magnetic stirring.

Depending on the molecular weight of the poly(propylene glycol) used, the proportions of trimethylamine and acryloyl chloride have to be adjusted (2.3 eq. and 2.1 eq. respectively per hydroxyl function).

The reaction was completed after 2 h. Triethylamine salts were removed by filtration and the product was washed several times with basic, acid and neutral water. The organic phase was dried with anhydrous sodium sulfate and filtrated. Final product (20.7 g, yield: 91%) was obtained after removal of the solvents under reduced pressure.

$^1$H NMR (CDCl$_3$, 300 MHz): 6.43-6.35 (2H, d, H—CH=CH—); 6.15-3.06 (2H, d, H—CH=CH—), 5.81-5.78 (2H, d, H—CH=CH—), 5.18-5.02 (2H, m, —C(O)—O—CH—CH$_2$—), 3.83-3.18 (42H, m, —CH(CH$_3$)—CH$_2$—), 3.83-3.18 (42H, m, —CH(CH$_3$)—CH$_2$—O—), 1.39-0.99 (42H, m, —CH(CH$_3$)—CH$_2$—O—).

Example 2: Preparation of the Embedding Medium of the Invention 2.1. One-Pot Solution Formulation 1

In a flask are introduced and stirred at room temperature, triethylene glycol dimethacrylate (TGdMA), poly(propylene glycol) diacrylate (PPGdA) and an initiator, preferably benzoin methyl ether and/or hydroxyl-2-methylpropiophenone, in a mass ratio 79/20/1. The final embedding medium 1 is stored away from light and/or heat.

Formulation 2

In a flask are introduced and stirred at room temperature, triethylene glycol dimethacrylate (TGdMA) and an initiator, preferably benzoin methyl ether and/or hydroxyl-2-methylpropiophenone, in a mass ratio 99/1. The final embedding medium 2 is stored away from light and/or heat.

Formulation 3

In a flask are introduced and stirred at room temperature, triethylene glycol dimethacrylate (TGdMA), hydroxyl PEG methacrylate and an initiator, preferably benzoin methyl ether and/or hydroxyl-2-methylpropiophenone, in a mass ratio 74/25/1. The final embedding medium 3 is stored away from light and/or heat.

Formulation 4

In a flask are introduced and stirred at room temperature, triethylene glycol dimethacrylate (TGdMA), poly(propylene glycol) diacrylate (PPGdA), a solution of silver nitrate (1.4 mM) and an initiator, preferably benzoin methyl ether and/or hydroxyl-2-methylpropiophenone, in a mass ratio 72.4/18.1/9/0.5. The final embedding medium 4 is stored away from light and/or heat.

2.2. Kit Comprising the Embedding Medium of the Invention

In first container are introduced and stirred at room temperature, triethylene glycol dimethacrylate (TGdMA), and poly(propylene glycol) diacrylate (PPGdA) in a mass ratio 79/20.

In second container is stored the initiator, preferably benzoin methyl ether and/or hydroxyl-2-methylpropiophenone.

The matrix precursor solution is obtained after mixing the contents of the first and second containers, preferably the mixture is carried out away from light and/or heat.

Part II—Preparation of an Electro-Conductive Imaging Material and its Imaging by Electron Microscopy Example 3: Process for Preparing a Biological Sample for Microscopy Analysis The aim is embedding a biological sample in order to provide a fluorescent and/or electro-conductive biological imaging material for electron microscopy. In this goal, the Applicant works out a process using the embedded medium 1 of example 2.

General Process

Step 1—Vitrification and/or Fixation/Dehydration of the Biological Sample

First, a biological sample is vitrified by any cryogenic methods well-known by the skilled artisan, and then introduced at −90° C. in a solvent which may be ethanol, methanol or acetone (the biological sample in the solvent is called "Freeze substitution cocktail"). Optionally, chemical fixatives and/or contrasting agents may be added. Examples of chemical fixatives may be osmium, osmium tetroxide, uranyl acetate, glutaraldehyde, and paraformaldehyde. Examples of contrasting agents may be uranyl acetate, lead derivatives, silver derivatives, osmium derivatives or tannic acid.

The biological sample is maintained during a period ranging from 1 mn to several days at −90° C. Then, the temperature is slowly increased until −40° C. and the freeze substitution cocktail is removed by successive washings with pure solvents. A dehydrated biological sample is obtained.

Step 2—Infiltration of the Embedded Medium 1

Second, the dehydrated biological sample obtained at step 1 is successively infiltrated with a mixture embedded medium/solvent until to be infiltrated with the embedded medium solution only. A composition comprising a dehydrated biological sample embedded in the matrix precursor solution of the invention is obtained.

Step 3—Polymerization—Preparation of the Electro-Conductive Biological Imaging Material The composition obtained at step 2 is then polymerized either by photopolymerization or by thermopolymerization. In the case of photopolymerization, the composition is initiated at −40° C. by UV irradiation during a period ranging from 24 h to 48 h. Then, the temperature is slowly increased to room temperature, always under UV irradiation. An extra 24 h of UV irradiation at room temperature is applied to achieve full polymerization inside the biological sample.

An electro-conductive and fluorescence preserving imaging material is obtained.

Step 4b (Optional)—Microtomy or Ultramicrotomy

The electro-conductive imaging material is optionally prepared by microtomy and/or ultra-microtomy, before its observation by electron microscopy.

Optional Further Step—Light Microscopy

In this process, a light microscopy analysis of the electro-conductive imaging material may be carried out at any one of the steps 1-4 before its observation by electron microscopy.

Part III—Observation by Electron Microscopy

Example 4: Microscopy Analysis

In order to demonstrate the superiority of the imaging material of the invention when used in electron microscopy, biological samples were prepared according to the protocol described in Example 3 in which the freeze cocktail comprises 0.05% of uranyl acetate, 0.01% of Glutaraldehyde, 1% of water and is carried out at a temperature ranging from −90° C. to −45° C.

Contrast

The aim is to compare the increase of contrast obtained from the embedding medium of the invention in comparison to Lowicryl® HM 20 resin, on HeLa cells, using both the same freeze substitution protocol (i.e. using the freeze cocktail comprising 0.05% of uranyl acetate, 0.01% glutaraldehyde and 1% water, at a temperature ranging from −60° C. to −45° C.).

The observations of HeLa cells have been carried out by transmission electron microscopy (TEM).

FIG. 1 shows that a better contrast is achieved with the material of the invention (see FIG. A) than the one obtained from Lowicryl® HM 20 resin (FIG. 1B).

Figure 2:
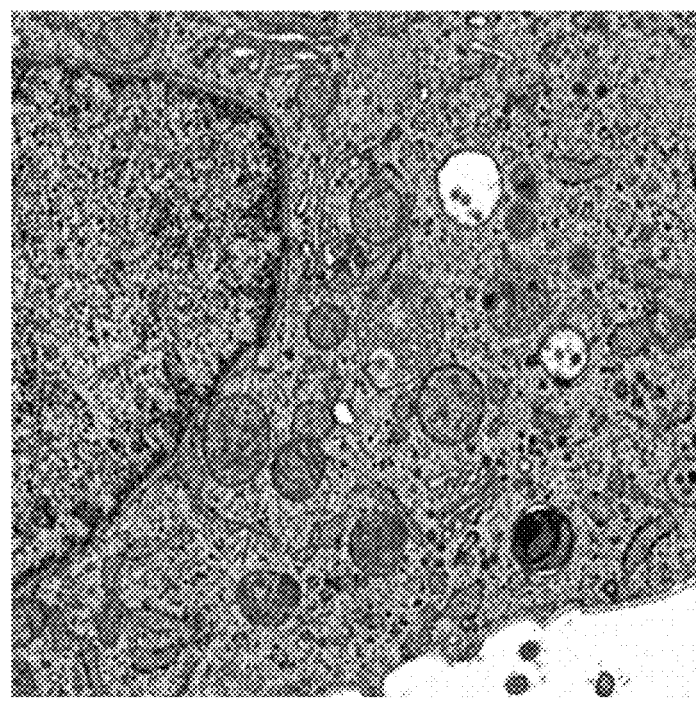
FIG. 2 is a cliché of HeLa cells embedded in the embedding medium of the invention, obtained by focused ion beam scanning electron microscopy (FIB-SEM).

The analysis of HeLa cells embedded in the material of the invention was also observed by scanning electron microscopy (SEM). FIG. 2 shows that the material of the invention makes it possible to finely visualize the structure of the cells embedded inside of said material.

Melanin Targeting

In this experiment, MNT1 cells (immortalized melanocyte line, MNT1 line) have been studied.

The observations of an imaging material of the invention comprising melanosomes and silver salts aggregates, have been carried out by electron microscopy.

Figure 3:
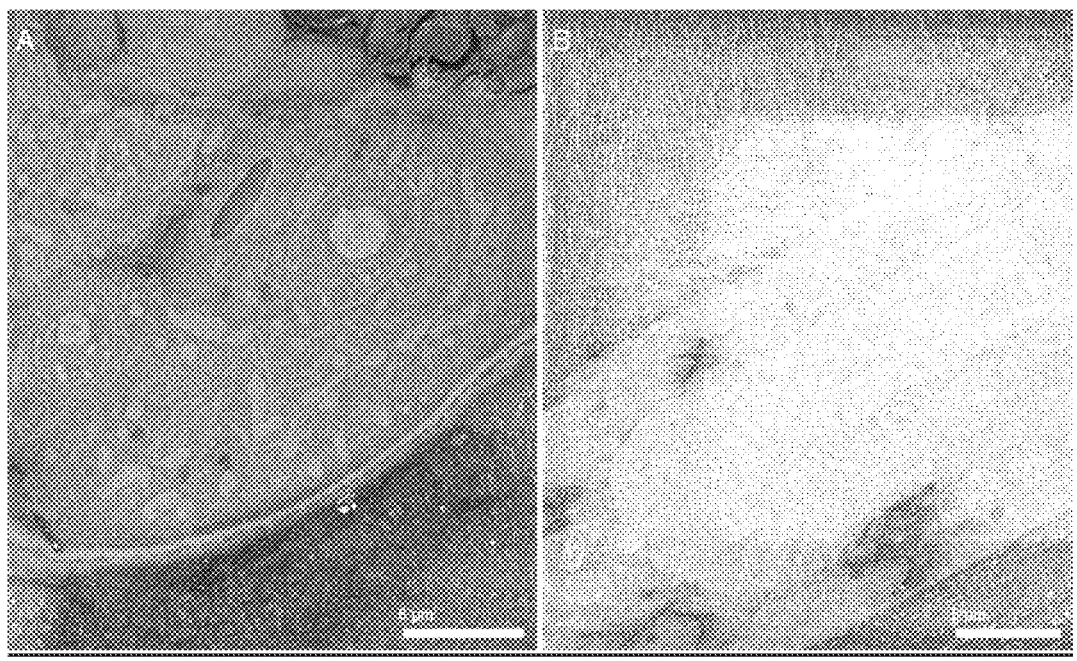
FIG. 3 is a comparison of two scanning electron microscopy (SEM 3View) cliché of the imaging material of the invention comprising *Caenorhabditis elegans* contrasted with 0.01% of uranyl acetate during freeze substitution. A is embedded in the medium of the invention, B is embedded in Lowicryl® resin. The first cliché shows sharp and homogeneous contrasts. The second shows significant charging seen as white spots and a square area used to focus the cliché. Electrons accumulate at the surface of the bloc, preventing sharp imaging.

Surprisingly, the corresponding cliché (FIG. 3A) shows that silver salts specifically accumulate in the biological structures.

Without willing to be bound by any theory, the Applicant submits that a specific reaction occurs during the microscopy study between silver salts incorporated in the imaging material of the invention, and the melanin aggregated to amyloid fibers of melanosomes.

In order to evidence this specific reaction, the same experiment has been carried out by replacing melanosomes by HeLa cells that do not express melanin.

The corresponding cliché (FIG. 3B) shows that silver salts are dispersed in the material but are not specifically located in the biological samples.

Consequently, the imaging material of the invention, especially the embedding medium, when comprising silver salts, allows specifically targeting biological samples containing melanin.

Fluorescence Presentation

The analysis of the preserved fluorescence of the MNT1 cells in the imaging material has also been carried out by Structured Illuminated Microscopy (SIM) (light microscopy).

Figure 4:
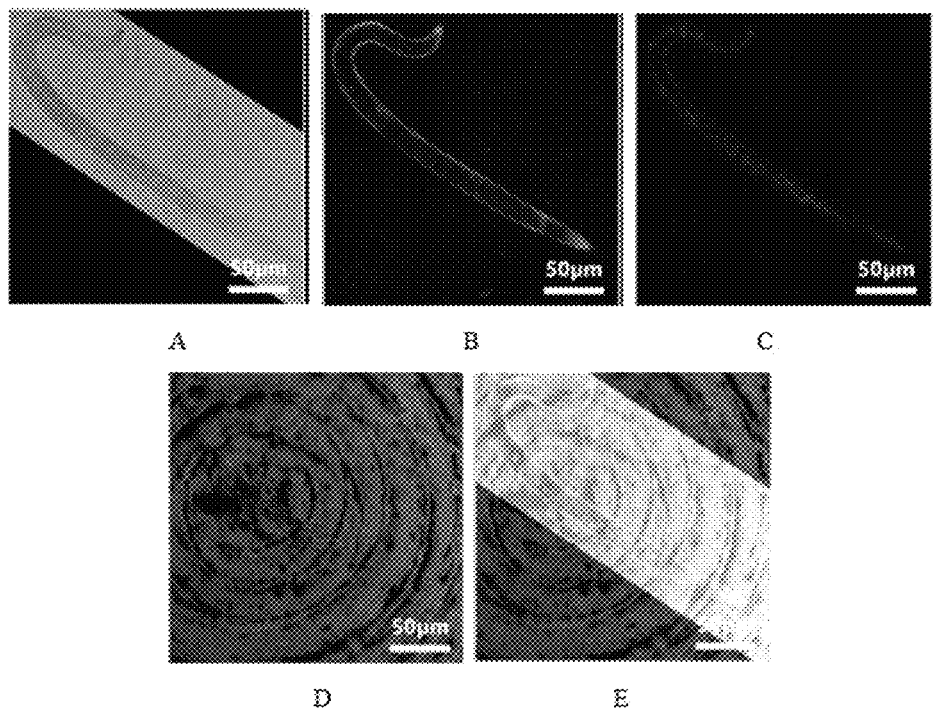
FIG. 4 is microscopy clichés of *Caenorhabditis elegans* embedded in the embedding medium of the invention. Cliché A was obtained by Scanning Electron Microscopy (SEM); Cliché B was obtained by Green Fluorescence protein (GFP) Cliché C was obtained by Red Fluorescence protein (RFP); Cliché D was obtained by Transmitted Light; and Cliché E is a MultiCanal image.
Figure 5:
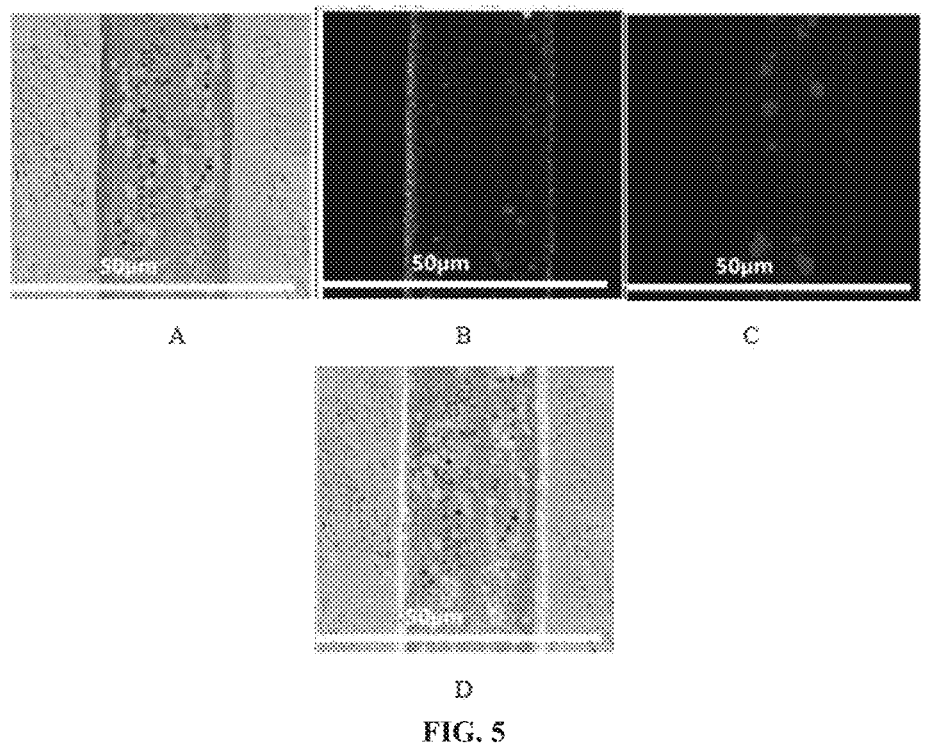
FIG. 5 is a zoom of fluorescence microscopy cliché of FIG. 4. Cliché A was obtained by Scanning Electron Microscopy (SEM); Cliché B was obtained by Green Fluorescence protein (GFP); Cliché C was obtained by Red Fluorescence protein (RFP); Cliché D is a MultiCanal image.

FIG. 4 and FIG. 5 show the efficient detection of the internal fluorescence of HeLa cells from the imaging material of the invention.

The invention claimed is:

1. An electro-conductive embedding medium for a biological sample comprising:
   from 60% to 99% wt. of a glycol dimethacrylate selected from alkylene glycol dimethacrylate and/or oligo(alkylene glycol) dimethacrylate;
   a polyalkylene glycol diacrylate or a polyalkylene glycol methacrylate; said polyalkylene glycol diacrylate or polyalkylene glycol methacrylate being optionally substituted by at least one hydrophilic group; and
   a radical polymerization initiator.

2. The electro-conductive embedding medium according to claim 1, further comprising at least one additive.

3. The electro-conductive embedding medium according to claim 2, wherein the additive comprises at least one heavy metal salt or lanthanide salt.

4. The electro-conductive embedding medium according to claim 1, wherein the polyalkylene glycol diacrylate or the polyalkylene glycol methacrylate is substituted by at least one hydrophilic group selected from hydroxyl, amino and oxo groups.

5. The electro-conductive embedding medium according to claim 1, wherein the glycol dimethacrylate is selected from ethylene glycol dimethacrylate, diethylene glycol dimethacrylate, triethylene glycol dimethacrylate, propylene glycol dimethacrylate and butylene glycol dimethacrylate.

6. The electro-conductive embedding medium according to claim 1, wherein the polyalkylene glycol diacrylate is selected from polyethylene glycol diacrylate, polypropylene glycol diacrylate and polybutylene glycol diacrylate.

7. The electro-conductive embedding medium according to claim 1, wherein the polyalkylene glycol methacrylate is selected from polyethylene glycol methacrylate, polypropylene glycol methacrylate and polybutylene glycol methacrylate; said polyalkylene glycol methacrylate being optionally substituted by at least one hydrophilic group.

8. The electro-conductive embedding medium according to claim 1, comprising:
   from 60% to 99% wt. of triethylene glycol dimethacrylate;
   from more than 0% to 38% wt. of polypropylene glycol diacrylate; and
   from 0.1% to 2% wt. of a radical polymerization initiator.

9. The electro-conductive embedding medium according to claim 1, comprising:
   from 60% to 99% wt. of triethylene glycol dimethacrylate;
   from more than 0% to 38% wt. of hydroxyl polyethylene glycol methacrylate; and
   from 0.1% to 2% wt. of a radical polymerization initiator.

10. The electro-conductive embedding medium according to claim 1, comprising:
    79% wt. of triethylene glycol dimethacrylate;
    20% wt. of polypropylene glycol diacrylate; and
    1% wt. of benzoin methyl ether.

11. The electro-conductive embedding medium according to claim 3, wherein the at least one heavy metal salt comprises osmium and/or uranyl acetate.

12. The electro-conductive embedding medium according to claim 1, further comprising at least one biological sample.

13. The electro-conductive embedding medium according to claim 12, wherein the biological sample is a vitrified and/or chemically fixed and/or dehydrated biological sample.

14. An electro-conductive imaging material comprising at least one biological sample embedded in a polymer matrix resulting from the polymerization of the embedding medium according to claim 1.

15. The electro-conductive material according to claim 14, preserving the internal fluorescence, the protein activity and/or the antigenic specificity of the embedded biological sample.

16. A method for imaging by microscopy a biological sample comprising the following steps:
    (i-1) fixing and/or dehydrating the biological sample;
    (ii) infiltrating on the biological sample of step (i-1) an electro-conductive embedding medium according to claim 1;
    (iii) polymerizing the mixture obtained at step (ii), resulting in an electro-conductive imaging material;
    (iv) imaging by light microscopy and/or electron microscopy the electro-conductive imaging material of step (iii).

17. The method according to claim 16, further comprising a step of microtomy or ultra-microtomy on the electro-conductive imaging material.

18. A method for imaging a biological sample by microscopy, comprising imaging either an electro-conductive medium according to claim 1 on which said biological sample is infiltrated or an electro-conducive imaging material embedded with said biological sample in a polymer matrix resulting from polymerization of said embedding medium.

19. A kit for preparing a biological sample to be imaged in microscopy, comprising:
    a first container comprising (a) a glycol dimethacrylate selected from alkylene glycol dimethacrylate and/or oligo(alkylene glycol) dimethacrylate; and (b) a polyalkylene glycol diacrylate or a polyalkylene glycol methacrylate, said polyalkylene glycol diacrylate or polyalkylene glycol methacrylate being optionally substituted by at least one hydrophilic group;
    a second container comprising radical polymerization initiator;
    or comprising:
    a container comprising (a) an glycol dimethacrylate selected from alkylene glycol dimethacrylate and/or oligo(alkylene glycol) dimethacrylate; (b) a polyalkylene glycol diacrylate or a polyalkylene glycol methacrylate, said polyalkylene glycol diacrylate or polyalkylene glycol methacrylate being optionally substituted by at least one hydrophilic group; and (c) a radical polymerization initiator; and
    a mixing means.

* * * * *